United States Patent
Schmieding et al.

(10) Patent No.: US 8,202,282 B2
(45) Date of Patent: Jun. 19, 2012

(54) KNOT PUSHER AND SUTURE RETRIEVER

(75) Inventors: Reinhold Schmieding, Naples, FL (US);
Robert M. Weber, Chino Hills, CA (US)

(73) Assignee: Arthrex, Inc., Naples, FL (US)

( * ) Notice: Subject to any disclaimer, the term of this patent is extended or adjusted under 35 U.S.C. 154(b) by 2208 days.

(21) Appl. No.: 10/357,449

(22) Filed: Feb. 4, 2003

(65) Prior Publication Data

US 2003/0220659 A1    Nov. 27, 2003

Related U.S. Application Data

(60) Provisional application No. 60/353,192, filed on Feb. 4, 2002.

(51) Int. Cl.
*A61B 17/04*    (2006.01)

(52) U.S. Cl. ........................................ 606/148; 606/139

(58) Field of Classification Search .................. 606/139, 606/144, 148, 205–211
See application file for complete search history.

(56) References Cited

U.S. PATENT DOCUMENTS

| | | | | |
|---|---|---|---|---|
| 4,890,615 A * | 1/1990 | Caspari et al. | ............... | 606/146 |
| 5,087,263 A * | 2/1992 | Li | ................. | 606/148 |
| 5,176,691 A * | 1/1993 | Pierce | ............... | 606/148 |
| 5,254,126 A * | 10/1993 | Filipi et al. | ................ | 606/146 |
| 5,257,637 A * | 11/1993 | El Gazayerli | ................ | 128/898 |
| 5,290,309 A * | 3/1994 | Kothe | ............ | 606/207 |
| 5,324,298 A * | 6/1994 | Phillips et al. | ............... | 606/148 |
| 5,507,756 A * | 4/1996 | Hasson | ............... | 606/139 |
| 5,536,273 A * | 7/1996 | Lehrer | .............. | 606/139 |
| 5,613,977 A * | 3/1997 | Weber et al. | ................ | 606/170 |
| 5,797,929 A * | 8/1998 | Andreas et al. | ............... | 606/148 |
| 6,045,561 A * | 4/2000 | Marshall et al. | ............... | 606/148 |
| 6,511,488 B1 * | 1/2003 | Marshall et al. | ............... | 606/148 |
| 6,517,552 B1 * | 2/2003 | Nord et al. | ................ | 606/144 |
| 7,918,867 B2 * | 4/2011 | Dana et al. | ................ | 606/144 |

* cited by examiner

*Primary Examiner* — Thomas C. Barrett
*Assistant Examiner* — Michael T Schaper
(74) *Attorney, Agent, or Firm* — Dickstein Shapiro LLP

(57) ABSTRACT

A hand instrument for retrieving suture and advancing a suture knot within a patient. The instrument has a shaft with proximal and distal ends. A hinged jaw in the form of a crabclaw disposed on the distal end of the shaft captures suture within a closed aperture formed by the jaws or is used to pinch the suture between the jaws. A hand mechanism disposed on the proximal end of the shaft opens and closes the jaw.

4 Claims, 5 Drawing Sheets

KNOT PUSHER AND SUTURE RETRIEVER

This application claims the benefit of U.S. Provisional Application Ser. No. 60/353,192, filed Feb. 4, 2002, the entire disclosure of which is incorporated herein by reference.

FIELD OF THE INVENTION

The present invention relates to a hand instrument for retrieving suture and advancing surgical knots down a length of a suture during a surgical procedure.

BACKGROUND OF THE INVENTION

Endoscopic suturing techniques and instruments have been developed to facilitate the suturing of tissue during endoscopic surgical procedures. Access to a surgical work site within a patient's body is normally provided through one or more portals formed directly in the patient's body or through one or more cannulas inserted into the patient's body through small incisions. A chosen surgical procedure is carried out by a surgeon through the use of elongated instruments inserted through these cannulas and it often becomes necessary to suture selected tissue at the surgical work site.

Since the work site is only accessible through a small portal or cannula and since it is very difficult to tie sutures within the body, various devices and techniques have been developed to enable the surgeon to tie sutures endoscopically. For example, some procedures enable the surgeon to pass suture material through selected tissue, form a surgical knot extracorporeally and then move the knot with a knot pusher through the portal or cannula into position adjacent the desired tissue to be sutured. Formation of the knot requires the surgeon to manually tie a knot on the suture strands after the suture is threaded through the selected tissues to be sutured. This procedure is often tedious and time-consuming. There is also a tendency for the knot to deform or collapse as the surgeon manually forces the knot down into its proper position. In addition, tying the knot in this manner is particularly difficult during endoscopic surgeries, where the visual field for the surgeon is severely limited by the narrow surgical area. As a result of these setbacks, there is a need for an improved method of tying a knot, as well as for surgical devices that will facilitate such method.

SUMMARY OF THE INVENTION

In one aspect, the invention provides a surgical hand instrument for retrieving suture within a patient and for advancing a slidable suture knot in a suture loop to close the loop. The surgical instrument of the present invention includes a shaft having a proximal end and a distal end, the shaft comprising an inner gear member disposed within an outer tubular member. A hinged jaw located at the distal end of the shaft is provided with a fixed jaw member attached to the outer tubular member of the shaft, and an opposing rotating jaw member attached to the inner gear member of the shaft. A hand mechanism, preferably including finger loops, is disposed on the proximal end of the shaft for rotating the inner gear member of the shaft and subsequently closing and opening the jaw. When closed, the hinged jaw forms a closed aperture that captures suture within it. Advantageously, the fixed and rotating jaws are sized so that the closed aperture of the jaw securely captures suture while still allowing free axial travel of the suture within the aperture. Alternatively, the fixed and rotating jaws can be closed together to pinch and retrieve a suture strand.

These and other features and advantages of the invention will become apparent from the following detailed description that is provided in connection with the accompanying drawings and illustrated exemplary embodiments of the invention.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The term "endoscopy" encompasses arthroscopy, laparoscopy, hysteroscopy, among others, and endoscopic surgery involves the performance of surgical procedures within a patient's body through small openings as opposed to conventional open surgery through large incisions.

Figure 1:
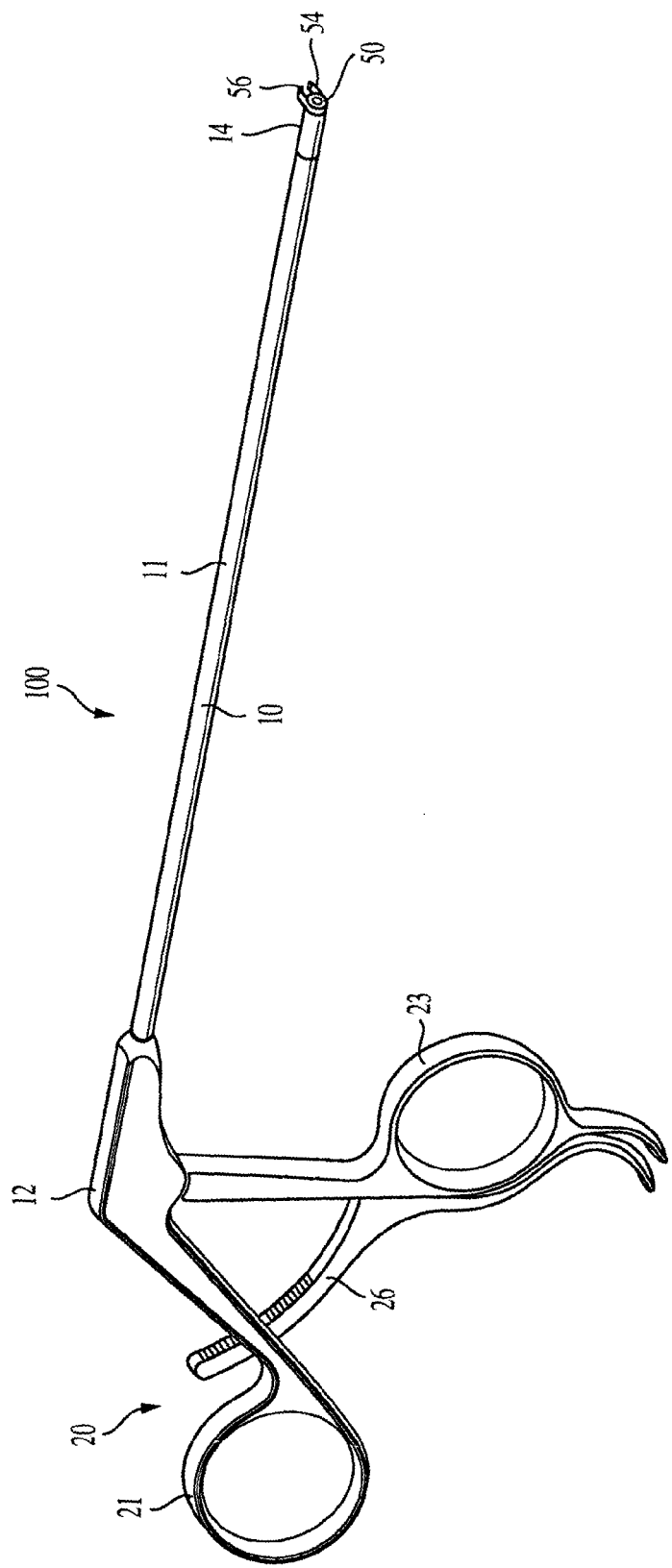
FIG. 1 illustrates a three dimensional view of a surgical instrument according to the present invention.
Figure 2:
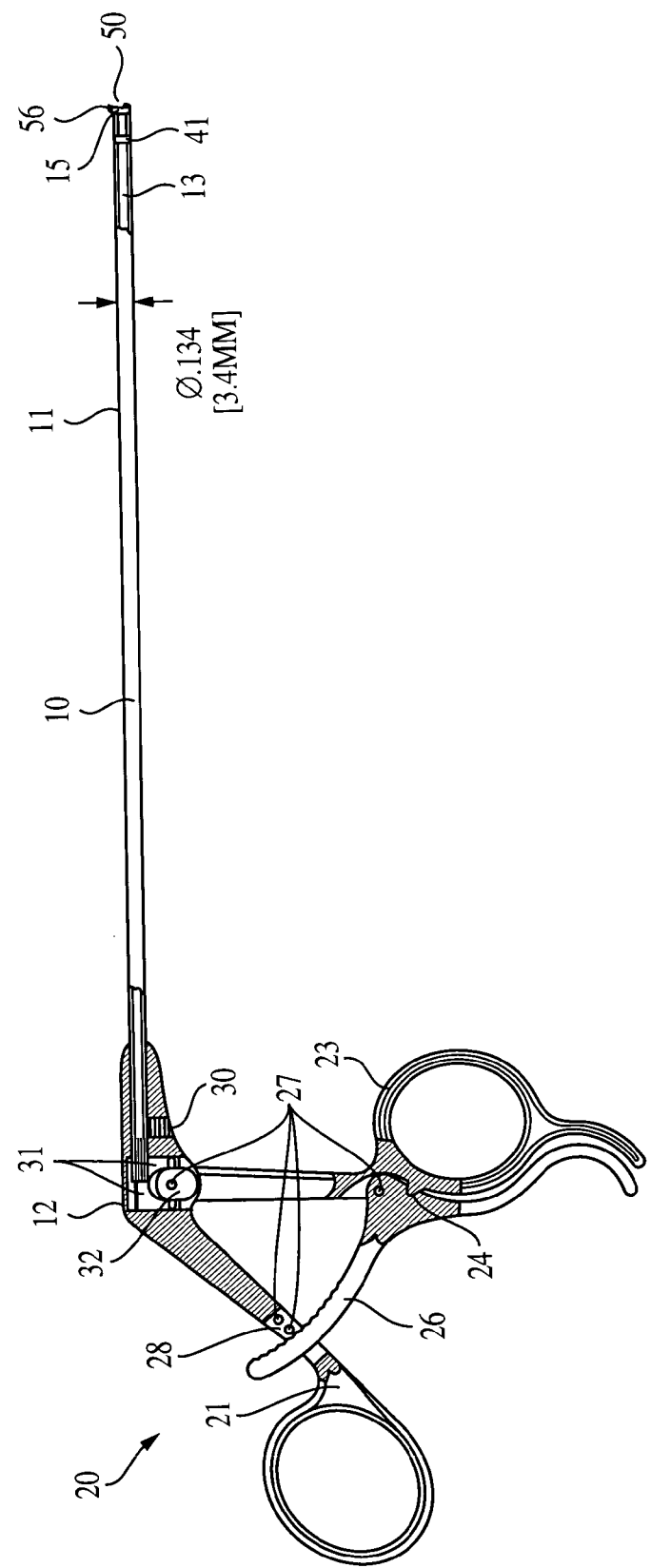
FIG. 2 illustrates a cross-sectional view of the surgical instrument of FIG. 1.
Figure 3:
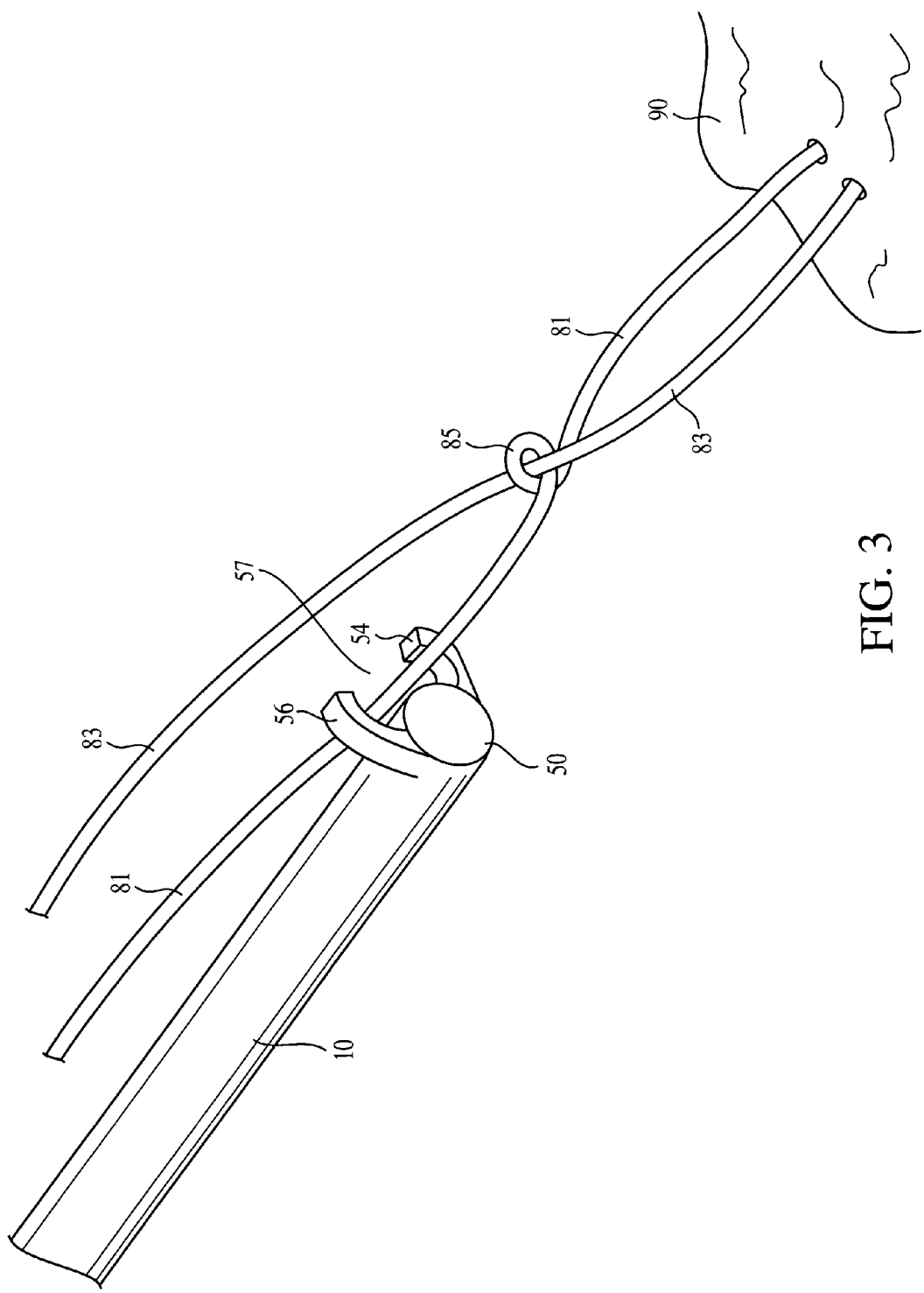
FIG. 3 illustrates a schematic view of a surgical site with two attached suture strands undergoing a knot tying and pushing operation according to a method of the present invention.

Referring now to the drawings, where like elements are designated by like reference numerals, FIGS. 1-3 illustrate a surgical instrument 100 of the present invention provided with a hinged annular jaw 50 in the form of a crabclaw to allow easy capture and release of a suture and free axial sliding of the suture through the closed jaw. As described in more detail below, when closed, the jaw 50 forms an aperture receiving a free end of a suture proximate to the knot, the aperture being large enough to slidably receive the free suture end but small enough to securely engage the knot and "push" the knot by advancing the instrument relative to the free suture end. The jaw is preferably configured to allow easy capture of the suture, even when the device is being manipulated through an access sleeve or trocar, and to ensure that the suture will not be inadvertently lost from the aperture as the knot is advanced.

The surgical instrument 100 preferably comprises an elongate, narrow diameter body or shaft assembly 10 suitable for use in remote procedures performed through percutaneous tissue punctures, such as vascular closures, laparoscopic and other minimally invasive procedures and the like. The shaft assembly typically has a length of about 5 cm to about 20 cm, preferably about 15 cm. The diameter of the shaft assembly is sufficiently small to facilitate introduction through access sheaths, trocars, and the like, typically being less than about 10 mm, preferably about 5 to about 7 mm.

As illustrated in FIGS. 1-2, the shaft assembly 10 has a proximal end 12 and a distal end 14 and includes an elongate outer tubular member 11 which houses a coaxial inner gear member 13. The inner gear member 13 has a diameter smaller than the diameter of the outer tubular member 11 and can freely rotate within the outer tubular member 11. As described in more detail below, the distal end 14 of the shaft is configured to engage and advance a slidable knot, while the proximal end 12 of the shaft has a handle assembly designed to facilitate manual manipulation of the device.

The shaft or body assembly 10 of the surgical instrument 100 has a round cross-sectional shape. The shaft or body assembly 10 is formed of a rigid, medically acceptable metal or plastic material, preferably stainless steel.

In a preferred embodiment, hinged jaw 50 is provided at the distal end 14 of the shaft assembly 10 of the knot pusher instrument. Although jaw 50 is depicted in the drawings at an angle of 90° relative to the shaft, the invention is not so limited, and the jaw may be provided at other angles. As illustrated in FIG. 1, the jaw 50 comprises a fixed jaw member 54 integrally attached to the outer tubular member 11 of the shaft assembly 10, and a rotating jaw member 56 secured to the inner gear member 13 of the shaft assembly 10 by a standard tip pin 15. Preferably, the fixed and rotating jaw members 54, 56 are formed of a relatively hard material to firmly engage the suture (when jaws 54, 56 are in the "closed" position) and permit smooth advancement of the suture knot. The rotating jaw 56 attached to the inner gear member 13 is actuated by rotating the inner gear member 13 relative to the outer tubular member 11 between an "open" configuration illustrated in FIG. 3 and a "closed" configuration illustrated in FIG. 4. When in the "closed" configuration, the fixed and rotating jaw members 54, 56 form a closed aperture 55 (FIG. 4) which allows a suture strand to be captured within it, while permitting the remaining portions of the suture outside of the radial opening to be tensioned, as desired.

As illustrated in more detail in FIG. 2, axial rotation and translation of the inner gear shaft 13 relative to the outer tubular member 11 is effected by an actuator or handle assembly 20 provided at the proximal end 14 of the shaft assembly 10. The actuator assembly 20 includes a stationary thumb loop 21 and a moveable finger loop 23 coupled to a rotary rack 31 and a grasper ratchet 26 engaged by spring 24.

Figure 4:
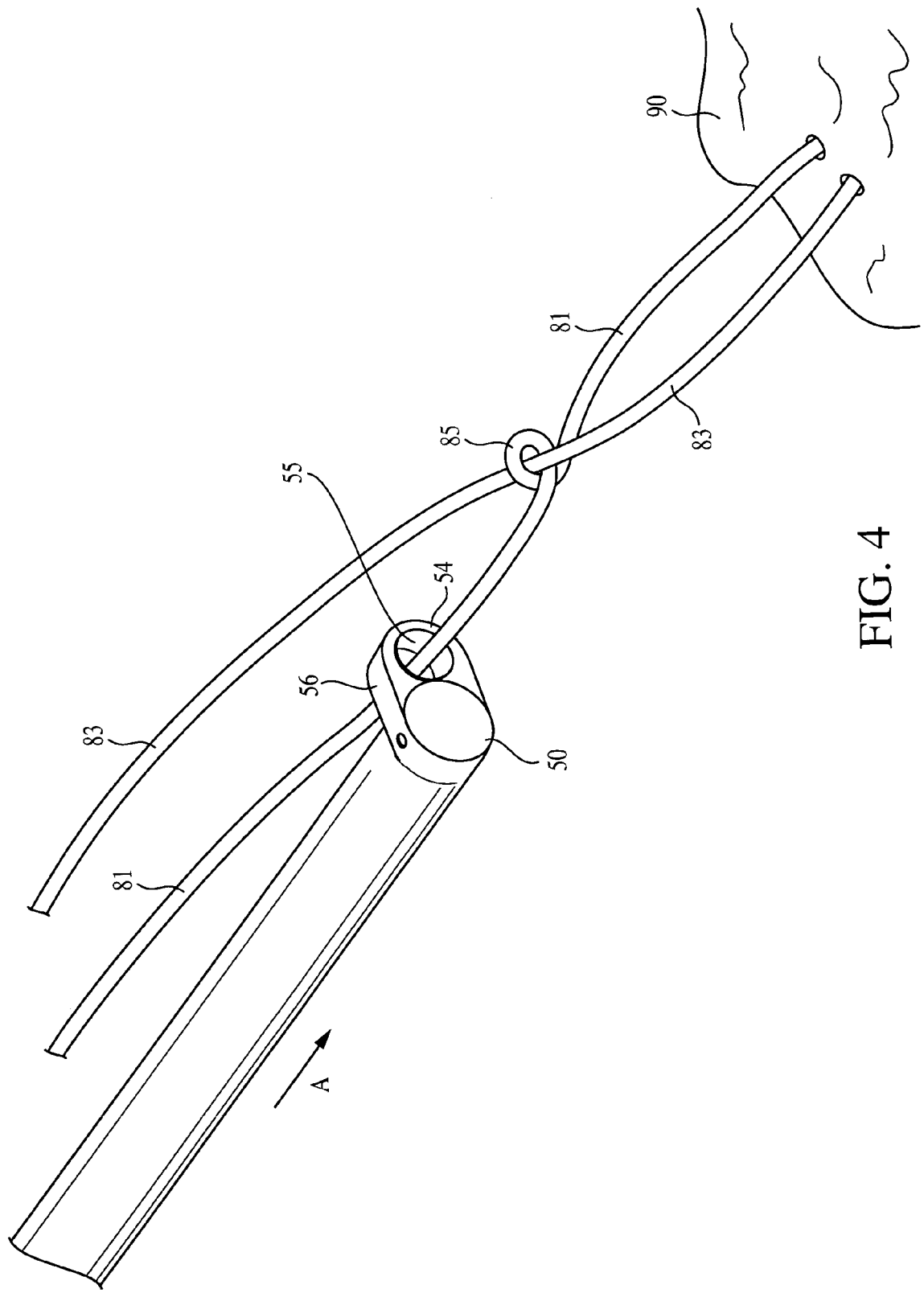
FIG. 4 illustrates the surgical site of FIG. 3 at a stage of operation subsequent to that shown in FIG. 3.

The jaw 50 may be opened to form a flared entrance 57 (FIG. 3) or closed to form the aperture 55 (FIG. 4) by rotating the inner gear shaft 13 which, in turn, causes the rotating jaw 56 to shift from the "closed" configuration of FIG. 4 to the "open" configuration of FIG. 3. The inner gear shaft 13 may be rotated in a first direction by manually applying force to the moveable finger loop 23 of the actuator assembly 20 to proximally retract the moveable finger loop 23 relative to the stationary thumb loop 21 (i.e., to separate the finger loops) and to cause therefore the rotating jaw 56 to open. In this manner, when the rotating jaw 56 shifts from the "closed" to the "open" configuration (FIG. 3), the jaws open and suture strand 81 is allowed to enter through flared entrance 57 of the radial opening 55 and is positioned between the rotating and stationary jaw members 56, 54.

Capture of the suture strand 81 within the radial opening 55 (FIG. 4) of the jaw 50 is accomplished by rotating the inner shaft 13 in a direction opposite to the first direction, by applying force to the moveable finger loop 23 of the actuator assembly 20 to advance the moveable finger loop 23 toward to the stationary thumb loop 21 (i.e., to close the hand trigger) and to cause, therefore, the rotating jaw 56 to close.

Although the above-described rotary mechanism is preferred to open and close the jaw, it should be understood that the invention can also be implemented with a traditional angled jaw hinge design. Moreover, although a hand trigger with finger and thumb loops is described above, a handle with standard sliding mechanisms or a spring loaded design can be used to actuate the jaws.

The hand instrument 100 of the present invention described above with reference to FIGS. 1-4 may be employed in various surgical medical procedures for closing and tightening suture loops during surgical procedures. For example, the knot pusher instrument 100 may be employed in endoscopic and arthroscopic procedures, including but not limited to arthroscopic rotator cuff repair, Bankhart shoulder repair, meniscal repair, and any orthopaedic procedure that requires tying a knot through soft tissue or bone tunnels, for example, or in conjunction with fixation devices, such as suture anchors. Additionally, the knot pusher instrument 100 may be utilized in other general surgical and specialty procedures that require suturing or knot tying at a remote site, such as inside the body. The instrument of the present invention may be also used in repairs where knot visibility or finger access can be limited. Finally, the jaws of the instrument may be used to pinch and retrieve suture in surgical procedures.

It will be appreciated, of course, that while the surgical instrument 100 may be particularly useful for performing remote procedures through access sheaths and trocars, it will also find use in open surgical procedures where its ability to capture suture will also provide advantages.

Figure 5:
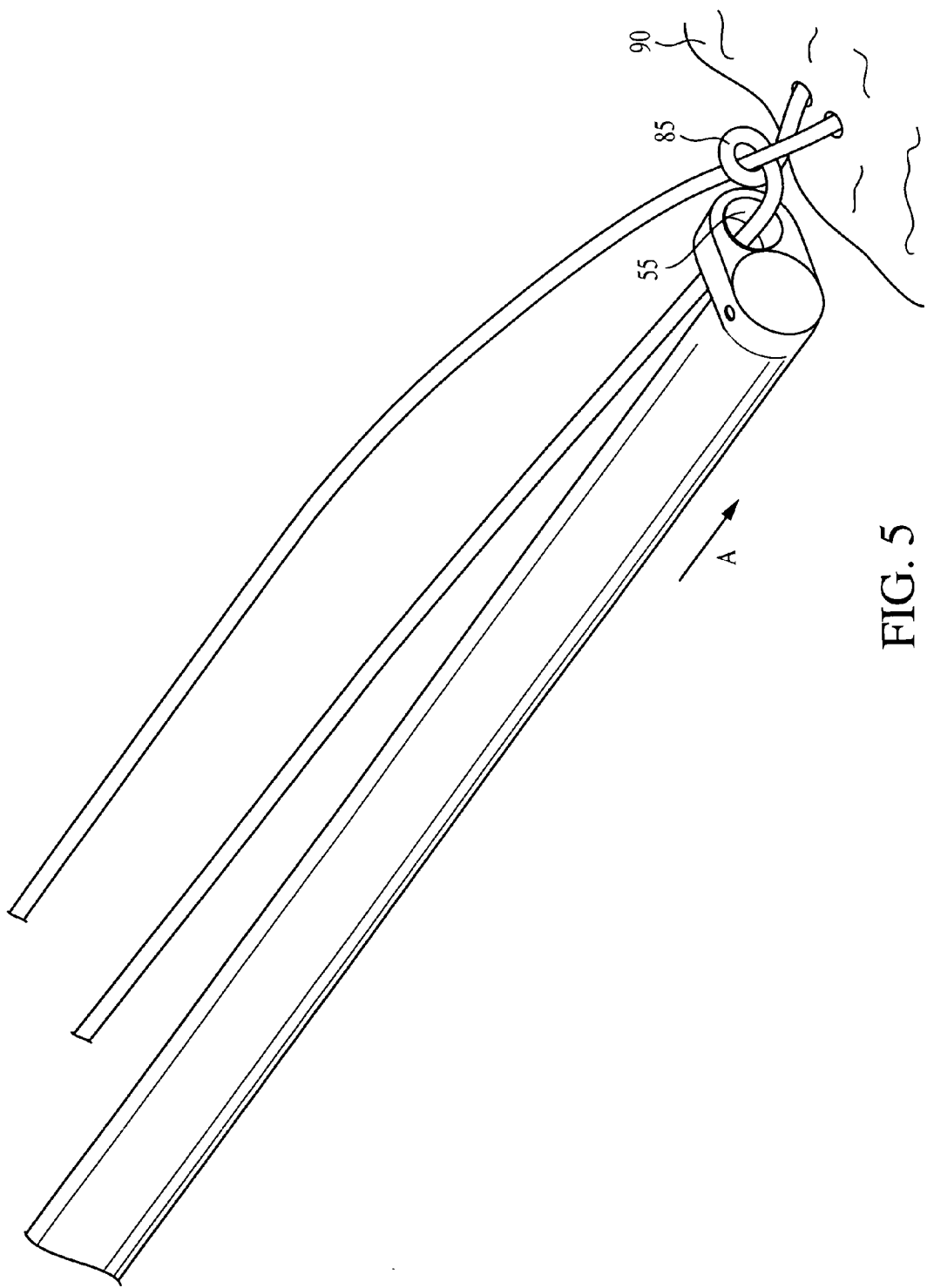
FIG. 5 illustrates the surgical site of FIG. 3 at a stage of operation subsequent to that shown in FIG. 4.

To better illustrate an exemplary surgical procedure conducted with the hand instrument 100 of the present invention, reference is now made to FIGS. 3-5, which illustrate a schematic view of a surgical site 90 provided with free ends of suture 81, 83 and knot 85 to be tightened and advanced in the proximity of to the surgical site 90. The hand instrument 100 is shown in FIG. 3 in the "open" position and in the proximity of the surgical site 90 and knot 85. The knot 85, which is a slidable knot or a square knot, can be tightened by pulling on the free ends 81, 83.

The method of the present invention begins by capturing a first free end 81 of the suture in the closed aperture 55, as illustrated in FIG. 4. The suture end 81 is captured by applying force to the moveable finger loop 23 of the handle assembly 20 to bring together the moveable finger loop 23 and the stationary thumb loop 21. After capturing the free suture end 81 within the aperture 55 of the "crabclaw" jaw 50, the user moves the instrument 100 forward to advance the knot 85 in the direction of arrow A (FIGS. 4-5) and in the close proximity of the surgical site 90. If desired, the jaw 50 can be locked in the "close" position by using grasper ratchet 26 in connection with grasper hook 28 and handle pin 27, disposed on the stationary thumb loop 21. Accordingly, during the advance of the instrument 100, for example, it is not necessary for the surgeon to maintain hand position at the finger loops of the instrument.

The knot 85 can then be tightened, typically by pulling on both free ends 81, 83, and the surgical instrument 100 can be subsequently withdrawn from any sheath or trocar, if used, and released from the suture end 81. The free ends of the suture 81, 83 can then be trimmed over the knot 85. Optionally, additional knot throws will be tied and advanced over the free suture end 81 using the surgical instrument 100.

Furthermore, the surgical instrument 100 may be employed to push consecutive half hitches formed around a suture end referred to as the post. Generally, a half hitch is started as a loop formed outside the body. The loop is then pushed through a portal in the skin to a remote site within the body. The instrument 100 captures the suture end and advances the loop distally along the post, so as to gather and secure soft tissue, for example, at the remote site of repair within the patient.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of advancing suture to tighten a knot, the suture having two suture strands extending from a surgical site at which the knot is to be positioned, the method comprising the steps of:

provid ing a knot pusher instrument comprising a shaft having a proximal end, a distal end, and a longitudinal axis, the shaft comprising an inner member located coaxially within an outer tube; a hinged jaw comprising a fixed jaw member located at the distal end of the shaft and integrally attached to, and coupled with, the outer tube and an opposing pivotable jaw member located at the distal end of the shaft and coupled with the inner member, wherein the fixed jaw member and the pivotable jaw member have a semicircular configuration; and a handle assembly located at the proximal end of the shaft and coupled with the pivotable jaw member;

positioning the hinged jaw, with the pivotable jaw member in an open position, proximal to the knot to be advanced;

actuating the handle assembly to move the opposing pivotable jaw member towards the fixed jaw member and from the open position to a closed position to form a closed aperture having a circular configuration and being perpendicular to the longitudinal axis of the shaft, to capture a suture strand of the knot with the closed aperture formed by the hinged jaw; and advancing the knot pusher instrument to move the knot toward the surgical site.

2. The method of claim 1 further comprising the step of disengaging the captured suture strand from the aperture of the hinged jaw.

3. The method of claim 1, wherein the step of actuating the handle assembly comprises rotating the pivotable jaw member by rotating the inner member of the shaft a predetermined amount.

4. The method of claim 1 further comprising the step of applying a tensile force to the captured suture strand while advancing the knot pusher instrument toward the surgical site.

* * * * *